US00PP20239P2

(12) United States Plant Patent
de Jong

(10) Patent No.: US PP20,239 P2
(45) Date of Patent: Sep. 1, 2009

(54) ***EUONYMUS* PLANT NAMED 'MARKIE'**

(50) Latin Name: *Euonymus fortunei*
Varietal Denomination: Markie

(76) Inventor: Gys Petrus de Jong, Newhaggard, Lusk, Dublin (IE)

( * ) Notice: Subject to any disclaimer, the term of this patent is extended or adjusted under 35 U.S.C. 154(b) by 11 days.

(21) Appl. No.: 12/215,291

(22) Filed: Jun. 26, 2008

(51) Int. Cl.
*A01H 5/00* (2006.01)

(52) U.S. Cl. ..... Plt./246
(58) Field of Classification Search ..... Plt./246
See application file for complete search history.

(56) References Cited

PUBLICATIONS

European Plant Breeders' Rights Application No. 2007/1037 filed Jun. 29, 2007. Copy of published information from European Plant Breeders' Rights Office web site attached. Plant material has not been made available to the public as of this file date.

*Primary Examiner*—Kent L Bell
(74) *Attorney, Agent, or Firm*—Audrey Charles

(57) ABSTRACT

A new and distinct cultivar of *Euonymus* plant named 'Markie', characterized by its immature leaves of green with yellow green-colored variegation, mature leaves of dark green with yellow green to yellow-colored variegation, large leaves, and moderately vigorous, spreading to broadly upright growth habit.

2 Drawing Sheets

Latin name of genus and species of plant claimed: *Euonymus fortunei.*
Variety denomination: 'Markie'.

BACKGROUND OF THE INVENTION

The present invention relates to a new and distinct cultivar of *Euonymus* plant botanically known as *Euonymus fortunei* and hereinafter referred to by the cultivar name 'Markie'.

The new *Euonymus* cultivar is a naturally-occurring whole plant mutation. The new cultivar was discovered and selected as a single plant within a population of plants of *Euonymus fortunei* during August 2005 in a controlled environment at Skerries, County Dublin, Ireland.

Asexual reproduction of the new *Euonymus* by cuttings in a controlled environment in Lusk, County Dublin, Ireland since August 2005, has shown that the unique features of the *Euonymus* are stable and reproduced true to type in successive generations.

SUMMARY OF THE INVENTION

The following characteristics of the new cultivar have been repeatedly observed and can be used to distinguish 'Markie' as a new and distinct cultivar of *Euonymus* plant:

1. Immature leaves of green with yellow green-colored variegation;
2. Mature leaves of dark green with yellow green to yellow-colored variegation;
3. Large leaves; and
4. Moderately vigorous, spreading to broadly upright growth habit.

Of the many commercially available *Euonymus* cultivars, the most similar in comparison to the new cultivar is the parent 'Emerald 'n Gold', U.S. Plant Pat. No. 2,231. However, in side by side comparisons of plants grown in Lusk, County Dublin, Ireland, plants of the new cultivar differ from plants of 'Emerald 'n Gold' in the following characteristics:

1. Plants of the new cultivar have a larger leaf than plants of 'Emerald 'n Gold';
2. Plants of the new cultivar have more leaf variegation than plants of 'Emerald 'n Gold'; and
3. Plants of the new cultivar have a foliage color different from plants of 'Emerald 'n Gold'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Markie'. The plants were grown for approximately 3 years in a 21 cm container in Lusk, County Dublin, Ireland in a glass-covered greenhouse.

The photograph on the first sheet is a side view of the overall growth and habit of 'Markie'.

The photograph on the top of the second sheet is a close-up view of the foliage of 'Markie'.

The photograph on the bottom of the second sheet is a close-up view of a mature leaf of 'Markie'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in April, 2008 under natural light conditions.

The following descriptions and measurements describe plants produced from cuttings from stock plants and grown in a glass-covered greenhouse under conditions comparable to those used in commercial practice. The plants were grown at April, 2008 under natural light conditions in Lusk, County Dublin, Ireland in 21 cm containers for approximately 3 years utilizing a soilless growth medium. Measurements and numerical values represent averages of typical plants.

Botanical classification: *Euonymus fortunei* cultivar 'Markie'.

Parentage:

*Parent.*—Unknown *Euonymus fortunei.*

Propagation:

*Type.*—Cuttings.

*Time to initiate roots during the summer with an average air temperature of 15° C. and an average soil temperature of 12° C.*—Approximately 21 days.

*Time to initiate roots during the winter with an average air temperature of 7° C., and an average soil temperature of 6° C.*—Approximately 42 days.

*Time to produce a rooted cutting during the summer with an average air temperature of 15° C., and an average soil temperature of 12° C.*—Approximately 42 days.

*Time to produce a rooted cutting during the winter with an average air temperature of 7° C., and an average soil temperature of 6° C.*—Approximately 84 days.

*Root description.*—Fine, moderately fibrous, and grayish-brown ranging from 199C to 199D.

*Rooting habit.*—Moderately dense and freely branching.

Plant description:

*Plant type and use.*—*Euonymus fortunei* is a flattened globular-shaped perennial shrub that can be used as a solitary garden plant or grouped.

*Commercial crop time.*—Approximately 1 year from a rooted cutting to saleable plant in an 11 cm pot.

*Growth habit and general appearance.*—Moderately vigorous, moderate growth rate, spreading to broadly upright growth habit.

*Size.*—Height from soil level to top of plant plane: Approximately 34.1 cm. Width: Approximately 46.2 cm.

*Branching habit.*—Freely basal branching, pinching not required but will improve branching. Quantity of lateral branches per plant: Approximately 74.

*Lateral branch.*—Appearance: Branches are dull in appearance and rounded. Strength: Strong. Length: Approximately 13.5 cm. Diameter: Approximately 2.0 mm. Length of central internode: Approximately 2.0 cm. Texture: Smooth, glabrous. Color of mature stem: 145A, occasionally tinged with 151A.

Foliage description:

*General description.*—Durability to stress: Moderate to high. Quantity of leaves per lateral branch: Approximately 14. Fragrance: None detected. Form: Simple. Arrangement: Opposite.

*Leaves.*—Shape: Broadly elliptic to broadly ovate. Margin: Crenate. Apex: Acute. Base: Short attenuate. Venation pattern: Pinnate. Length of mature leaf: Approximately 3.5 cm. Width of mature leaf: 2.8 cm. Texture of upper and lower surfaces: Slightly rugose, glabrous, slightly glossy. Color of upper surface of young foliage: N144A with an irregular central blotch of 141A or 143A and venation of 145C to 145D. Color of lower surface of young foliage: 145A with an irregular central blotch of 147C and venation of 144A to 144B. Color of upper surface of mature foliage: 153D to 11A or 13B with an irregular central blotch of 139A to 189A and venation of 145C to 145D. Color of lower surface of mature foliage: 153D to 11A with an irregular central blotch of 146B to 146C and venation of 144A to 144B.

*Petioles.*—Length: Approximately 6.0 mm. Diameter: Approximately 1.0 mm. Color: 145B.

Flower and seed production: Not available, flower and seed production have not been observed.

Disease and pest resistance: Plants of the new *Euonymus* have been observed to have high outdoor tolerance to downy mildew, aphids and red spider mite.

Weather tolerance: Plants of the new *Euonymus* have been observed to be hardy to USDA zone 6 and tolerate high temperatures to at least 35° C., and to demonstrate very excellent tolerance to rain and wind effects.

What is claimed is:

1. A new and distinct cultivar of *Euonymus* plant named 'Markie', substantially as herein shown and described.

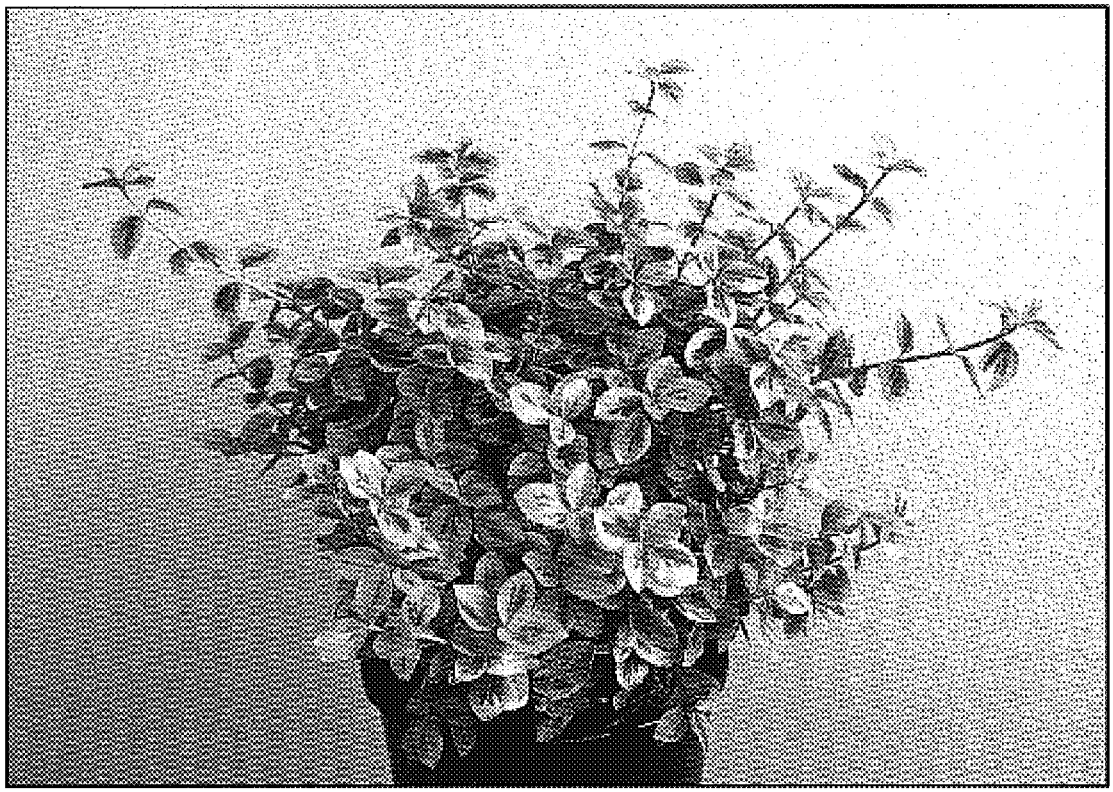

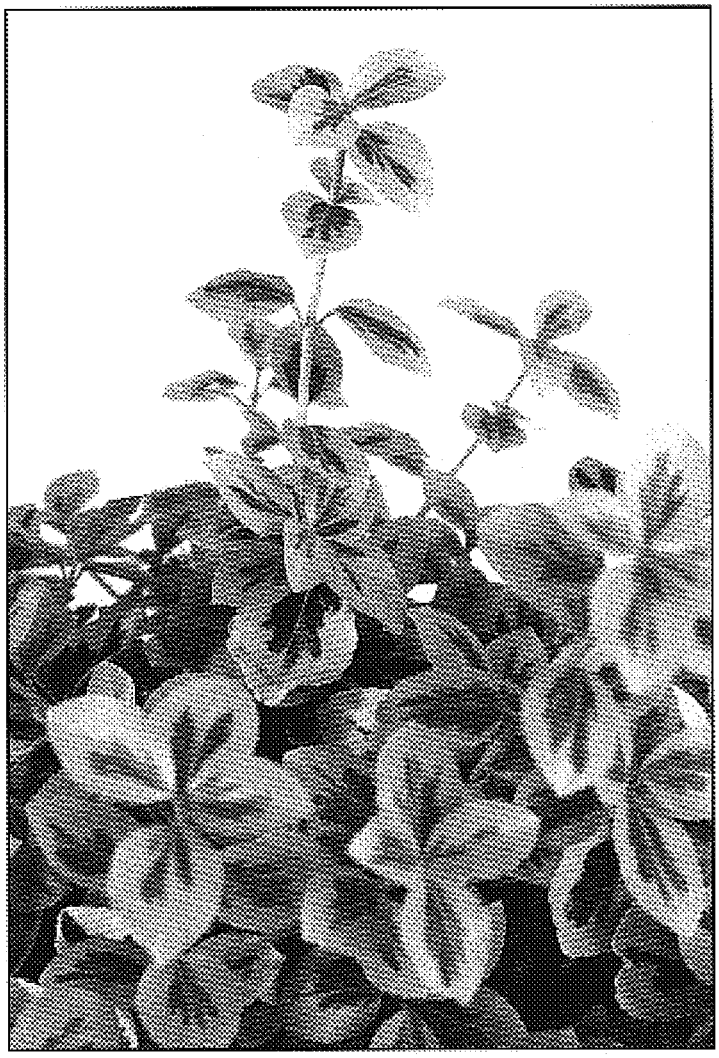
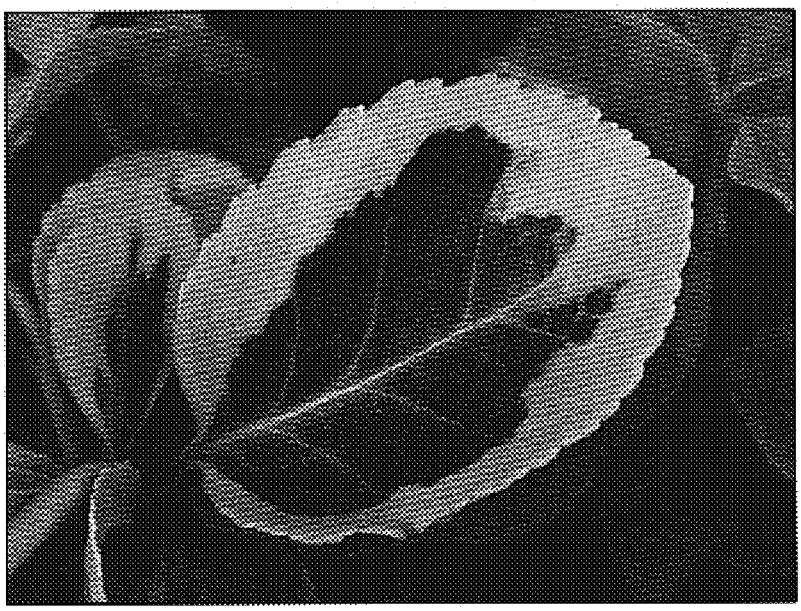

* * * * *